(12) United States Patent
Hamilton, Jr.

(10) Patent No.: US 9,033,889 B2
(45) Date of Patent: *May 19, 2015

(54) METHODS, ASSEMBLIES, AND DEVICES FOR POSITIONING A CATHETER TIP USING AN ULTRASONIC IMAGING SYSTEM

(71) Applicant: AngioDynamics, Inc., Latham, NY (US)

(72) Inventor: William C. Hamilton, Jr., Queensbury, NY (US)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/146,779

(22) Filed: Jan. 3, 2014

(65) Prior Publication Data

US 2014/0121503 A1     May 1, 2014

Related U.S. Application Data

(63) Continuation of application No. 13/347,786, filed on Jan. 11, 2012.

(51) Int. Cl.
*A61B 8/14*     (2006.01)
*A61M 25/01*     (2006.01)
*A61B 8/08*     (2006.01)
*A61B 8/12*     (2006.01)
*A61M 25/09*     (2006.01)
*A61B 19/00*     (2006.01)

(52) U.S. Cl.
CPC .......... *A61M 25/0108* (2013.01); *A61B 8/0841* (2013.01); *A61B 2019/5263* (2013.01); *A61B 2019/5429* (2013.01); *A61B 8/12* (2013.01); *A61M 25/09* (2013.01)

(58) Field of Classification Search
CPC ............ A61B 8/02; A61B 8/06; A61B 8/461; A61B 8/463; A61B 8/465; A61B 8/466; A61B 8/0883; A61B 8/0891; A61B 8/13; A61B 8/5246; A61B 8/488; A61B 8/5223; A61B 8/0841; A61B 8/12; A61B 2019/5263; A61B 2019/5429; A61M 25/0108; A61M 25/09
USPC .................................................. 600/437–469
See application file for complete search history.

(56) References Cited

U.S. PATENT DOCUMENTS

| | | | | |
|---|---|---|---|---|
| 4,951,677 A | * | 8/1990 | Crowley et al. | 600/463 |
| 5,421,338 A | * | 6/1995 | Crowley et al. | 600/463 |
| 5,452,359 A | * | 9/1995 | Inanaga et al. | 381/310 |
| 5,588,436 A | * | 12/1996 | Narayanan et al. | 600/459 |
| 5,954,649 A | * | 9/1999 | Chia et al. | 600/424 |

(Continued)

*Primary Examiner* — Sanjay Cattungal
(74) *Attorney, Agent, or Firm* — Peter J. Flora

(57) ABSTRACT

A catheter assembly includes an elongated member having an ultrasonic beacon disposed adjacent to a distal end portion of the elongated member, a power supply releasably attachable adjacent to the proximal end of the elongated member, and a catheter. The distal end portion of the elongated member with the ultrasonic transmitter is inserted into an anatomical structure of the human body, and the ultrasonic transmitter is powered by the power supply. Using conventional medical ultrasonography equipment, a technician is able to observe and/or track on a display an image of the internal structure of the human body and an image such as an illuminated bright spot representing the energized ultrasonic beacon. After locating the elongated member, the power supply is removed, and the catheter is slid onto the elongated member to locate the catheter tip. Thereafter, the elongated member is removed.

15 Claims, 12 Drawing Sheets

(56) References Cited

U.S. PATENT DOCUMENTS

| | | | | |
|---|---|---|---|---|
| 6,128,958 | A * | 10/2000 | Cain | 73/626 |
| 6,215,231 | B1 * | 4/2001 | Newnham et al. | 310/371 |
| 6,233,477 | B1 * | 5/2001 | Chia et al. | 600/424 |
| 6,246,899 | B1 * | 6/2001 | Chia et al. | 600/424 |
| 6,259,941 | B1 * | 7/2001 | Chia et al. | 600/424 |
| 7,722,549 | B2 * | 5/2010 | Nakao | 600/564 |
| 8,167,805 | B2 * | 5/2012 | Emery et al. | 600/439 |
| 8,226,675 | B2 * | 7/2012 | Houser et al. | 606/169 |
| 8,372,009 | B2 * | 2/2013 | Emery et al. | 600/439 |
| 2006/0116605 | A1 * | 6/2006 | Nakao | 600/566 |
| 2007/0213616 | A1 * | 9/2007 | Anderson et al. | 600/448 |
| 2007/0233185 | A1 * | 10/2007 | Anderson et al. | 606/213 |
| 2007/0239000 | A1 * | 10/2007 | Emery et al. | 600/437 |
| 2008/0234711 | A1 * | 9/2008 | Houser et al. | 606/169 |
| 2010/0010393 | A1 * | 1/2010 | Duffy et al. | 601/2 |
| 2011/0230763 | A1 * | 9/2011 | Emery et al. | 600/439 |
| 2011/0230796 | A1 * | 9/2011 | Emery et al. | 601/2 |
| 2012/0109023 | A1 * | 5/2012 | Emery et al. | 601/2 |
| 2012/0269676 | A1 * | 10/2012 | Houser et al. | 422/1 |
| 2013/0006229 | A1 * | 1/2013 | Delaney | 606/15 |
| 2013/0012839 | A1 * | 1/2013 | Emery et al. | 601/2 |

* cited by examiner

METHODS, ASSEMBLIES, AND DEVICES FOR POSITIONING A CATHETER TIP USING AN ULTRASONIC IMAGING SYSTEM

FIELD OF THE INVENTION

The present invention relates generally to positioning a catheter tip such as within a human body. More specifically, the invention relates to methods, assemblies, and devices for positioning a catheter tip using an ultrasonic imaging system.

BACKGROUND OF THE INVENTION

Medical professionals commonly use catheters for gaining prolonged access to an area within the body. Once the catheter tip is positioned at the target location, treatments such as antibiotics, chemotherapy, pain medicine, and nutrition can be administered. However, if the catheter tip is improperly positioned during insertion, or if the catheter tip migrates out of position after insertion, various risks arise, including a fluid infusion that causes pain or injury to the patient, complications due to increased thrombosis rates, delays in therapy, catheter malfunction and additional costs.

The general standard for proper catheter insertion depends on the type of catheter and the type of treatment. For example, peripherally inserted central catheters (or PICC lines) are commonly inserted into a brachial, cephalic or basilic vein in the arm and advanced through the venous system towards the superior vena cava. Current medical standards recommended that the distal tip of the catheter terminate in the lower ⅓ of the superior vena cava, close to the junction of the superior vena cava and the right atrium. However, since PICCs are commonly inserted into a vein in the arm and advanced through the venous system to reach the superior vena cava, the PICC line tip may be inadvertently positioned in a non-target area, such as the internal jugular or subclavian vein. Further, even if a PICC is property inserted, the catheter tip could later shift out of position if for example the patient coughs violently, moves a lot, or experiences severe vomiting.

Catheter tip location techniques have improved the ability of medical professionals to verify the location of the catheter tip. One technique uses fluoroscopy to confirm tip location. Fluoroscopy provides the operator with real-time images of the patient's anatomy using a fluoroscope. Another technique uses electromagnetic detection and a stylet having an electromagnetic sensor placed inside the lumen of the catheter tip. Electromagnetic systems use an external device positioned directly over the internal target area for generating a magnetic field outside of the body. The electromagnetic sensor on the stylet is then inserted into the body through the catheter lumen and measures when the magnetic flux is at its greatest. A monitor indicates to the user when the electromagnetic sensor on the stylet is centered underneath the external device. In a variation of this technique, the external device senses the electromagnetic field. Electrocardiogram technology is also used determine catheter tip location by measuring the change of the P wave as the catheter progresses down the superior vena cava.

U.S. Pat. No. 5,161,536 issued to Vilkomerson et al. disclose an ultrasonic imaging system employing a processing circuit which enables the imaging system to accurately display the location of an element in a body by utilizing a transducer which provides an electric signal when an ultrasonic wave impinges thereon. The electric signal is processed to determine the maximum amplitude signals during an entire frame of the ultrasonic imaging system. The signals are characterized in terms of the line at which the signal appears or the ray at which the signal appears and the pixel or location along that line. The information regarding ray and pixel serves as X-Y coordinates enabling one to accurately locate the element and transducer on the displayed image by intensifying the display at that location or by adding color or by producing some other visual effect such as blinking, and so on.

There is a need for further methods, assemblies, and devices for positioning a catheter tip within a human body.

SUMMARY OF THE INVENTION

In a first aspect, the present invention provides a method for positioning a catheter tip of a catheter within a human body. The method includes obtaining an elongated member having a proximal end portion and a distal end portion. An ultrasonic beacon is operably attached to the distal end portion of the elongated member, and a power supply releasably attaches adjacent to the proximal end portion of the elongated member and releasably electrically connects to energize the ultrasonic beacon. The distal end portion of the elongated member having the ultrasonic beacon is inserted into an anatomical structure of the human body. An ultrasonic transmitter/receiver is positioned adjacent to the outer surface of the human body and to the location of the inserted distal end portion of the elongated member, and the ultrasonic beacon is powered with the power supply. A display of an ultrasound image is observed of the internal structure of the human body and an image representing the energized ultrasonic beacon based on ultrasonic waves received by the ultrasound transmitter/receiver. The power supply is disconnected from a proximal end portion of the elongated member, and the catheter tip is inserted over the proximal end portion of elongated member. The catheter tip is positioned relative to the elongated member, and the elongated member is removed from the catheter.

In a second aspect, the present invention provides a catheter assembly comprising an elongated member having a proximal end portion and a distal end portion, an ultrasonic beacon is operably attached to the distal end portion of the elongated member, a power supply is releasably attachable adjacent to the proximal end portion of the elongated member and releasably electrically connects to the ultrasonic beacon, and a catheter includes a proximal end portion and a distal end portion. The distal end portion of the catheter being slideably receivable over the proximal end portion of the elongated member when the power supply is detached from the elongated member.

In a third aspect, the present invention provides a method for repositioning a catheter tip of a catheter within a human body. The method includes obtaining an elongated member having a proximal end portion and a distal end portion. The distal end portion has an ultrasonic beacon, and the proximal end portion having a power supply operably electrically connectable to energize the ultrasonic beacon. The distal end portion of the elongated member having the ultrasonic beacon is inserted in a catheter disposed in anatomical structure of the human body with the ultrasonic beacon disposed adjacent to the catheter tip. Ultrasonic transmitter/receiver is positioned adjacent to the human body and to the location of the inserted distal end portion of the elongated member, and the ultrasonic beacon is powered with the power supply. A display is observed of an ultrasound image of the internal structure of the human body and an image representing the energized ultrasonic beacon based on ultrasonic waves received by the ultrasound transmitter/receiver. The observed image representing the energized ultrasonic beacon is tracked as the distal end portion of the elongated member and the catheter tip of the catheter are repositioned at a desired location. The elongated member is then removed from the catheter.

In a fourth aspect, the present invention provides a method for positioning a catheter tip of a catheter within a human body. The method includes obtaining an elongated member having a proximal end portion and a distal end portion. An ultrasonic beacon is operably attached to the distal end portion of the elongated member, and a power supply is operably attached to the proximal end portion of the elongated member and operably electrically connected to energize the ultrasonic beacon. The distal end portion of the elongated member with the ultrasonic beacon is inserted into an anatomical structure of the human body. An ultrasonic transmitter/receiver is positioned adjacent to the outer surface of the human body and to the location of the inserted distal end portion of the elongated member with the ultrasonic beacon, and the ultrasonic beacon is powered with the power supply. A display is observed of an ultrasound image of the internal structure of the human body and an image representing the energized ultrasonic beacon based on ultrasonic waves received by the ultrasound transmitter/receiver. The catheter tip is slid along the elongated member in the human body, the catheter tip is positioned relative to the elongated member, and the elongated member is removed from the human body and from the catheter.

In a fifth aspect, the present invention provides an ultrasonic device for use within a human body. The device includes an elongated member having a proximal end, a distal end, and one or more ultrasonic beacons. A power supply is operably attached to the proximal end portion of the elongated member and operably attached to the one or more ultrasonic beacons.

BRIEF DESCRIPTION OF THE DRAWINGS

The subject matter which is regarded as the invention is particularly pointed out and distinctly claimed in the concluding portion of the specification. The invention, however, may best be understood by reference to the following detailed description of various embodiments and the accompanying drawings in which:

DETAILED DESCRIPTION OF THE INVENTION

Figure 1:
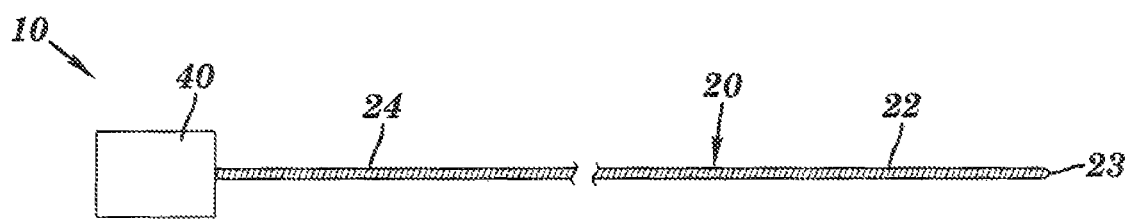
FIG. 1 is a side elevational view of one embodiment of an energizable guidewire in accordance with an aspect of the present invention.

The present invention can be understood more readily by reference to the following detailed description, the examples included therein, and to the drawing figures. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

As explained in greater detail below, the present invention in one aspect is directed to methods and apparatus for positioning and/or confirming a desired location of a catheter tip of a catheter in a body such as a human body using an energizable guidewire having an ultrasonic beacon and using an ultrasonic imaging system to locate and/or trace the movement of the distal end of the energizable guidewire.

As shown in FIG. 1, one exemplary embodiment of an energizable guidewire 10 in accordance with an aspect of the present invention includes an elongated member 20 and a releasably attachable power supply 40. Elongated member 20 may include a distal end portion 22 and a proximal end portion 24. Distal end portion 22 includes a distal end 23. The elongated member may be a flexible elongated member made from a medical grade flexible material having a diameter of about 0.014 inch to about 0.038 inch and smaller than the diameter of a lumen or passageway in a catheter as described below. The regions along the flexible elongated member 20 can vary in stiffness, depending on the application. For example, the guidewire may be a wire coil formed from a helix of wire having a generally constant outer diameter or varying outer diameter. While the present description refers to an energizable guidewire, it will be appreciated the present invention may be suitably configured as an energizable stylet, inner catheter, guide catheter, or other medical component that may be inserted into the catheter lumen.

Figure 2:
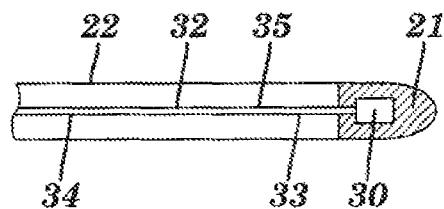
FIG. 2 is an enlarged side elevational view, partially cut away, of the distal end of the energizable guidewire of FIG. 1.

As best shown in FIG. 2, adjacent to distal end portion 22 of the elongated member is an ultrasonic beacon 30 such as a piezoelectric transmitter, crystal, or film. Ultrasonic beacon 30 is passive in that it emits ultrasound waves but does not receive. For example, the beacon emits identifying signals related to its position so that the information so produced can be used, as explained below, for guidance orientation, position, or location. Plurality of wires 32 and 34 may be operably electrically connected to the ultrasonic beacon. For example, a distal end portion 33 of wire 32 may be operatively connected to ultrasonic beacon 30, and a distal end portion 35 of wire 34 may be operatively connected to ultrasonic beacon 30. As described below, the proximal end of the wires may be connected to a suitable driver and electrical power supply. Distal end portion 22 of the elongated member may be filled with gel or other suitable potting material 21 around beacon 30 to reduce the likelihood of an air cavity attenuating or preventing transmission of ultrasonic waves from beacon 30.

Figure 3:
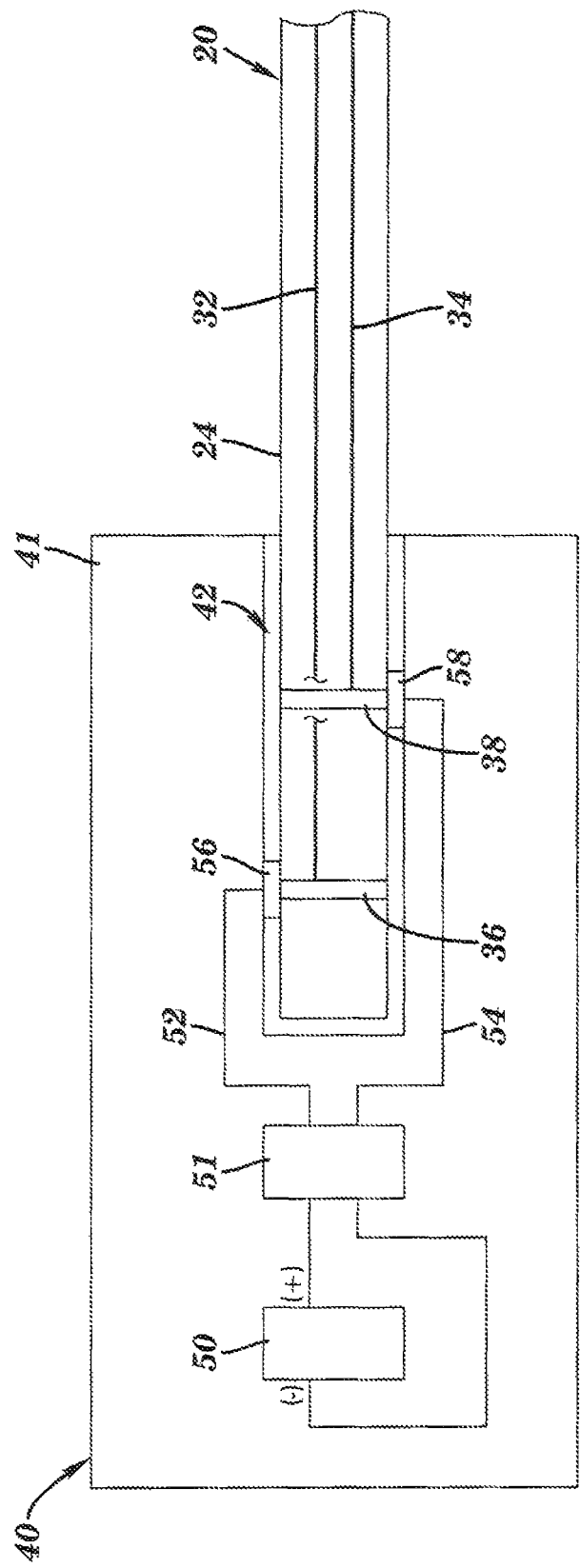
FIG. 3 is an enlarged side elevational view, partially cut away, of the power supply and proximal end of the energizable guidewire of FIG. 1.

With reference to FIG. 3, power supply 40 may include a housing 41 which is releasably attachable to proximal end portion 24 of elongated member 20. For example, housing 41 may include a cavity 42 sized and configured for receiving therein proximal end portion 24 of elongated member 20. Proximal end portion 24 of elongated member 20 may include a plurality of spaced-apart contacts 36 and 38 which extend circumferentially around an outer peripheral surface of proximal end portion 24 of elongated member 20 and which are operably connected to wires 32 and 34 in elongated member 20.

Housing 41 may include a chamber for containing a battery 50 and suitable connectors for connecting the different polarities of battery 50 via suitable wires for connecting battery 50 to a suitable driver 51 such as an oscillator for driving ultrasonic beacon 30 (FIG. 2). Driver 51 maybe operably connected to wires 52 and 54 for supplying electric power to contacts 56 and 58, respectively, positioned in cavity 42 of housing 41. Contacts 56 and 58 may be spaced a similar distance as contacts 38 and 38 so that when proximal end portion 24 of elongated member 20 is inserted in cavity 42 of power supply 40, electrical power is supplied to ultrasonic beacon 30 (FIG. 2). In addition, cavity 42 may be sized so that when proximal end portion 24 of elongated member 20 inserted in cavity 42, a compression force is applied between contacts 56 and 58 and contacts 36 and 38, respectively. It will be appreciated that other suitable means for releasably connecting the proximal end of the elongated member to the housing, and other suitable means for electrically connecting the power supply to the ultrasonic transmitter may be employed.

Figure 4:
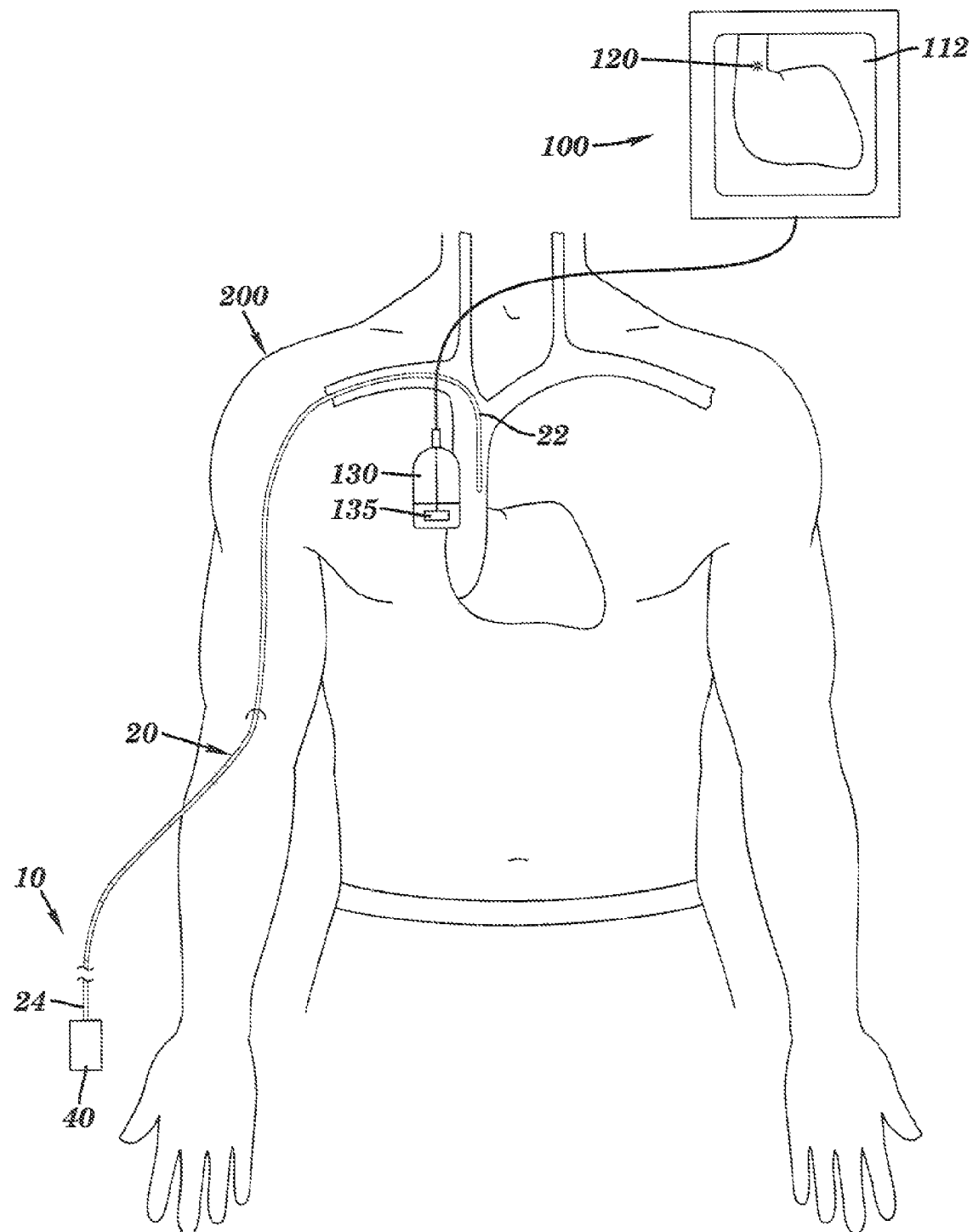
FIG. 4 is a diagrammatic illustration of one embodiment of a system for positioning the tip of the energized guidewire of FIG. 1 in a human body in accordance with an aspect of the present invention.

FIG. 4 illustrates one embodiment of the initial steps for positioning a catheter tip of a catheter in a body such as a human body using energizable guidewire 10 in accordance with an aspect of the present invention. Initially, for example, an introducer needle, dilator, and splitable sheath (not shown) may be used to gain access to a vein of a patient. Distal end portion 22 of elongated member 20 may be introduced into the splittable sheath and positioned at a desired location in the patient. When introducing the distal end portion of the elongated member, the releasably attachable power supply may be attached or disconnected from the proximal end of the elongated member.

Under one exemplary technique for accessing the vessel, a venipuncture is performed with the introducer needle, and guidewire 10 is inserted through the needle and advanced into the vessel. Once guidewire 10 is positioned, the introducer needle can be retracted off guidewire 10. Under another exemplary technique for accessing the vessel, a venipuncture is performed with the introducer needle, and a small guidewire is inserted through the needle and advanced into the vessel. The introducer needle is retracted off the small guidewire, and a dilator and splittable sheath assembly is advanced over the small guidewire and into the vessel. Once the dilator and splittable sheath assembly is properly introduced into the vessel, the small guidewire and dilator can be withdrawn from the vessel, leaving the splittable sheath for providing access to the vessel. Guidewire 10 can then be inserted into the lumen of the splittable sheath and into the vessel. The splittable sheath can be removed by retracting it over guidewire 10 while splitting the sheath outward, and removing it away from guidewire 10 completely.

As described in greater detail below, a conventional ultrasonic imaging system 100 may be employed to confirm the location of the distal end 22 of guidewire 10, or monitor and/or track the location of distal end 22 of energized guidewire 10, which may be inserted into a vein, an artery, or other body part of a patient under investigation and moved by a practitioner. For example, the guidewire may be initially positioned without monitoring the progress or location of the distal end 22 or with monitoring the progress or location of the distal end 22 as described below.

As shown in FIG. 4, an ultrasonic imaging system 100 generally includes a display 112, and a scanning head 130. Ultrasonic imaging systems enable imaging of internal structures of the body generally without the use of harmful forms of radiation. Display 112 enables the practitioner or user of the system to visualize the portion of a patient's body that is being scanned. The scanning head 130 may be a single hand held unit which the physician manually moves about the outer surface of the body of a patient to thereby perform imaging of the internal structure of the body. Scanning head 130 includes an ultrasonic transducer or transmitter/receiver 135, and utilizes emitted ultrasonic waves to provide a clear scan picture of the volume of tissue and other structures under investigation.

In addition, as shown in FIG. 4, energized ultrasonic beacon 30 (FIG. 2) disposed in distal end 22 of guidewire 10 is capable of providing a real-time observable image 120 on display 112 such as a bright illuminated spot on the displayed real-time image of the internal structure of the body. For example, ultrasonic beacon 30 converts electrical signals received from power supply 40 into ultrasound waves which are then picked up by transmitter/receiver 135 of scanning head 130 which then converts the wave pattern into electrical signals which are transmitted to and imaged on display 112.

As will be appreciated, the ultrasonic waves emitted from energized ultrasonic beacon 130 (FIG. 2) is automatically detected and processed by ultrasonic imaging system 100 along with the image of internal structure of the body. Scanning head 130 provides a beam of ultrasonic waves which beam is directed into the body 200 of a typical patient under investigation. The internal structure of the body is imaged by detection of the reflected waves along with the image of emitted ultrasonic waves from ultrasonic beacon 30 (FIG. 2). For example, transmitter/receiver 135 performs two functions. First, it acts as a standard ultrasound transducer which transmits and receives ultrasonic waves to create the image of the target area, e.g. the heart and the superior vena cava. Second, it then also receives the ultrasonic waves from the beacon 30 and converts them into a visual image or illuminated dot on the ultrasound display. Thus, no physical connection is needed between guidewire 10 and ultrasonic imaging system 100. Thus, a physician or technician can monitor and locate distal end 22 of energized guidewire 10 by viewing display 112 to determine the progress and/or location of distal end 22 of energized guidewire 10.

Figure 5:
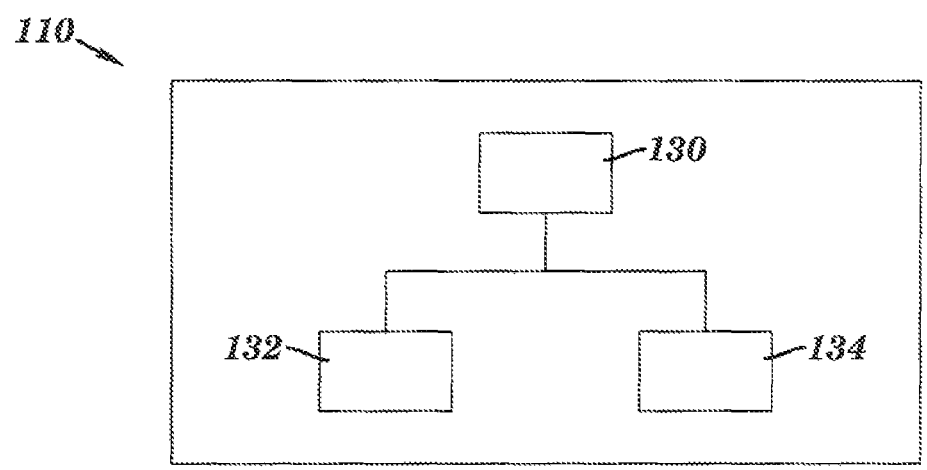
FIG. 5 is a block diagram of the ultrasonic imaging system of FIG. 4.

FIG. 5 is a block diagram of one embodiment of ultrasonic imaging system 100 which may include, for example, a computing unit or processor 130, one or more data storage units 132 such as memory, and one or more input/output devices 134 such as display 112 (FIG. 4) and transmitter/receiver 135 (FIG. 4).

Figure 6:
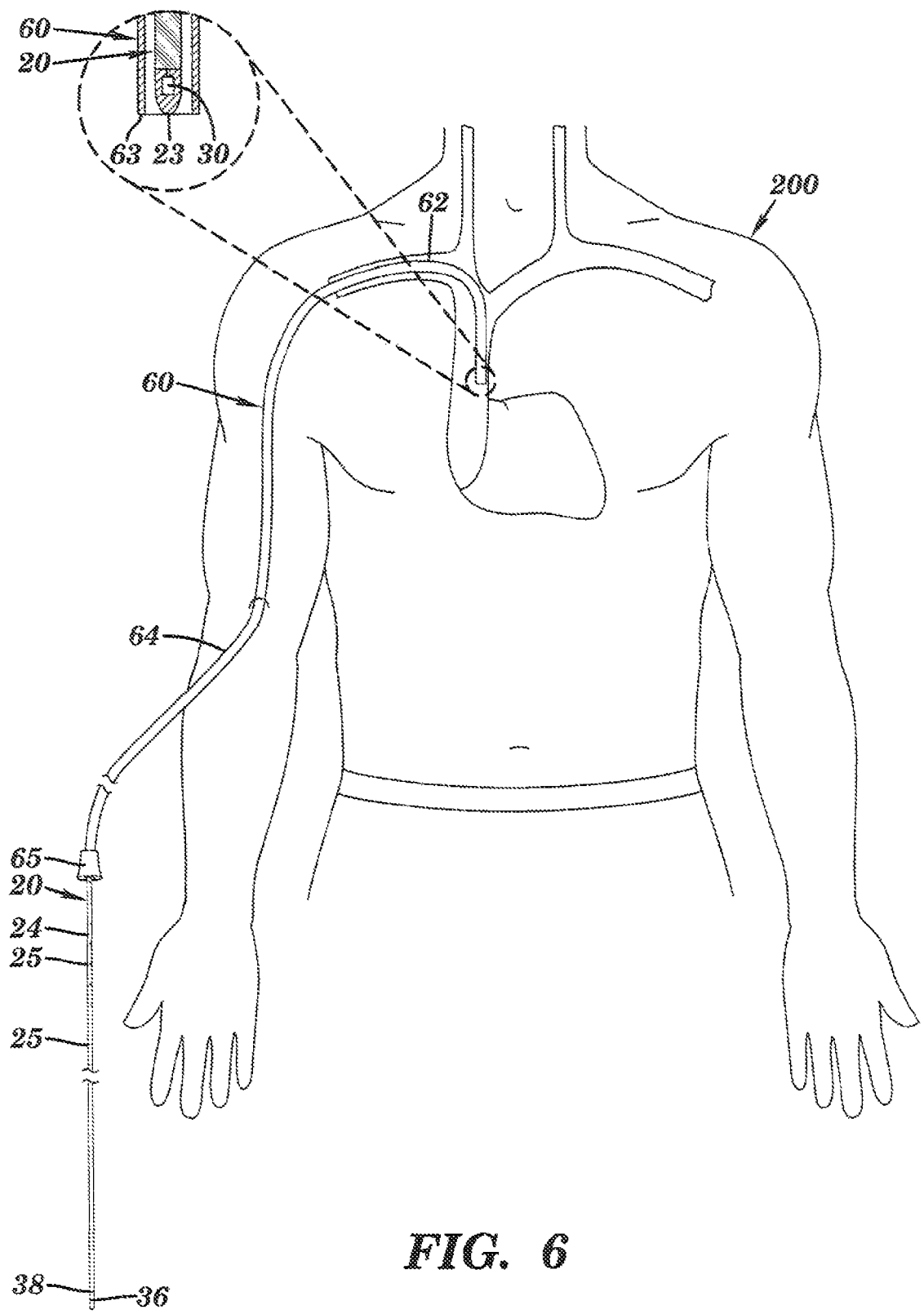
FIG. 6 is a diagrammatic illustration similar to FIG. 4 of a catheter slid onto the guidewire in FIG. 4.

With reference to FIG. 6, once the distal end of the guidewire is positioned at the desired location in the body, power supply 40 (FIG. 4) is disconnected from proximal end 24 of elongated member 20. The needle or splitable sheath may be suitably removed from the patient and from the elongated member 20. A catheter 60 may include a distal end portion 62 and a proximal end portion 64. Distal end portion 62 includes a tip 63. Tip 63 of a catheter 60 is inserted over proximal end 24 of elongated member 20, and advanced over the guidewire into the body. Suitable guide markings 25 may be used to position tip 63 of catheter 60 relative to and adjacent to distal end 23 of elongated member 20. As an example, the proximal edge of the catheter hub 65 may be aligned with one of a plurality of guide marking 12 on the guidewire so that the catheter tip 63 is positioned flush with distal end 23 of elongated member 20 and adjacent beacon 30. For example, the markings may be spaced every 1 or 2 centimeters and numbered corresponding to the distance from the distal end. If the catheter has a length of 50 centimeters, the catheter hub can be aligned with the 50 cm marking on the elongated member to position the catheter tip even with the distal end of the elongated member. From the present description, while the ultrasonic beacon is illustrated as being disposed adjacent to the distal end of the elongated member, it will be appreciated that the beacon need not be positioned at the distal end of the elongated member. The beacon may be positioned at any location along the elongated member. For example, the beacon may be positioned away from the distal end of the elongated member which may be beneficial for other procedures such as when attempting to locate a desired anatomical site in which the distal end not may extend past a treatment site.

Figure 7:
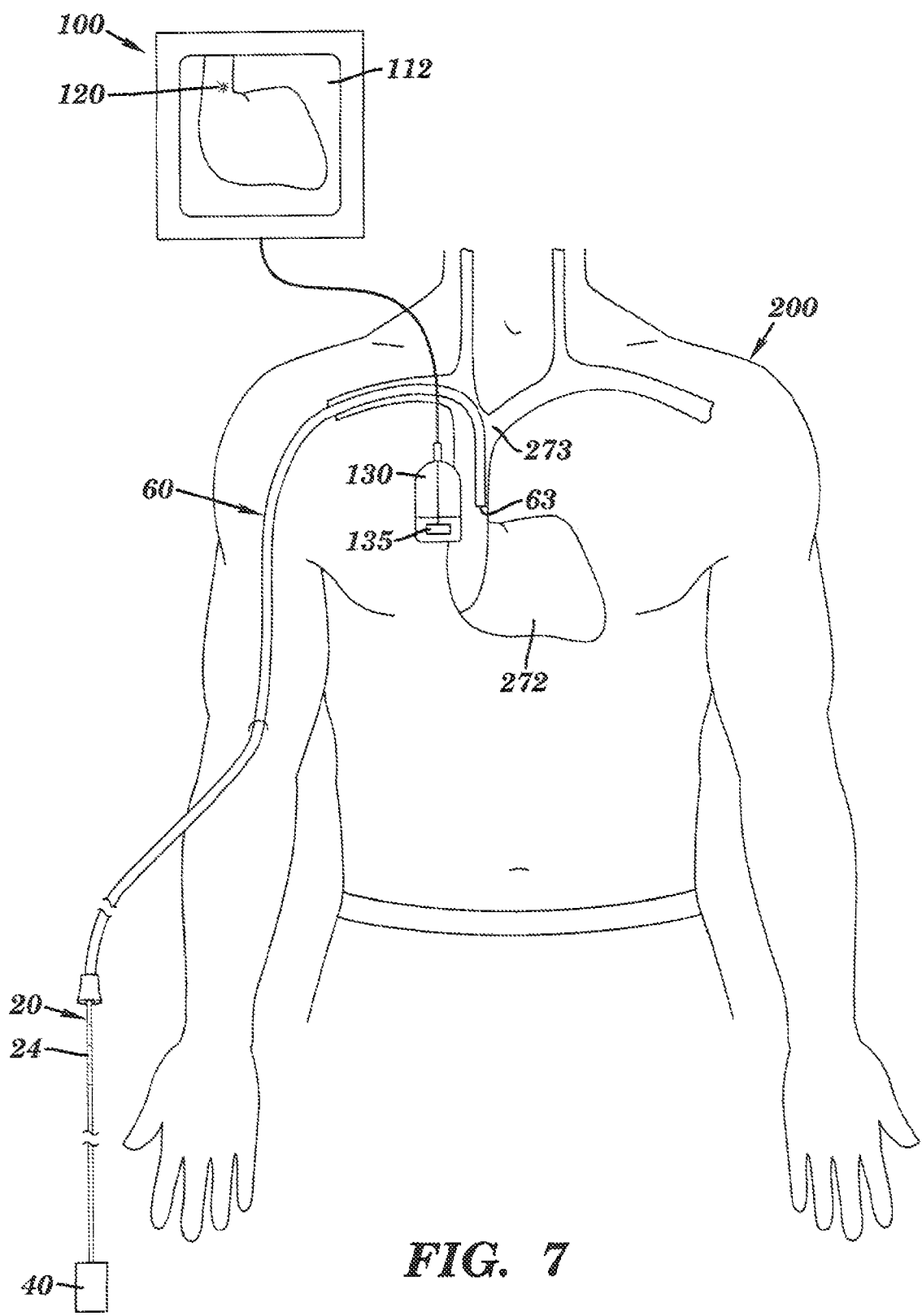
FIG. 7 is a diagrammatic illustration similar to FIG. 6 of confirming the location of the tip of the catheter in a human body using the energizable guidewire.

As shown in FIG. 7, power supply 40 may be reconnected to the proximal end 24 of elongated member 20 and using ultrasonic imaging system 100 and display 112, the observable image 120 displayed on the display may be used to confirm that the location of the tip 63 of catheter 60 is at the desired location in the body. For example, the target location for catheter tip 63 may be just outside of the heart 272 in the lower ⅓ of the superior vena cava 273. Further, when the catheter tip is positioned in a non-target location (e.g. the internal jugular vein or the subclavian vein), the observable image 120 displayed on the display may be used to confirm the non-target location of the tip 63 of catheter 60 in the body, and allow the operator to reposition the distal end of the elongated member and the catheter tip.

Figure 8:
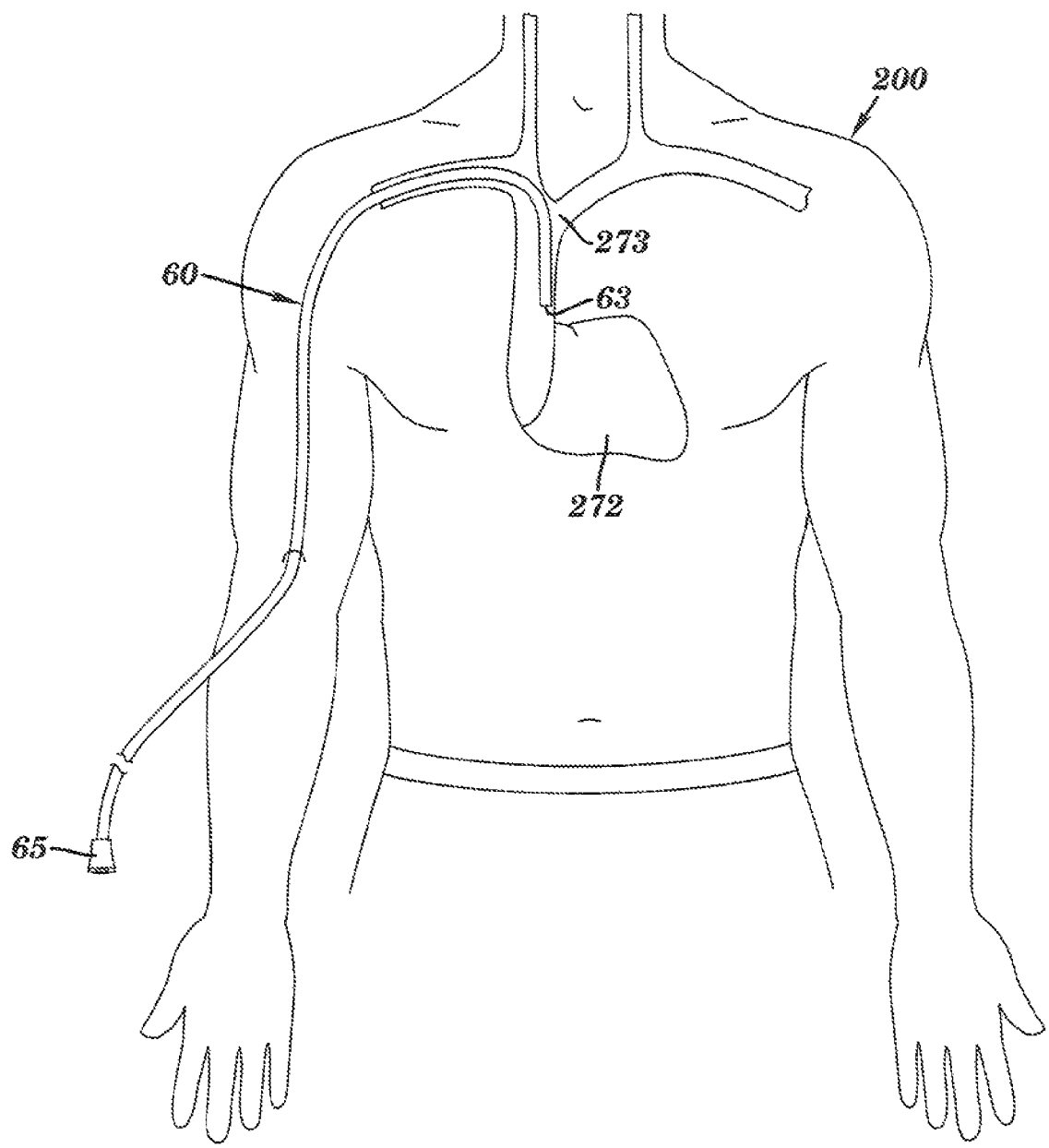
FIG. 8 is a diagrammatic illustration, similar to FIG. 7, in which the guidewire is removed from the catheter.

As shown in FIG. 8, the proximal end of catheter 60 may be secured relative to the human body (not shown in FIG. 8), and the guidewire (not shown in FIG. 8) may be completely removed from catheter 60. In the event that the catheter tip become mispositioned after initial insertion, e.g., if the catheter or patient moves a lot after insertion, the guidewire may be reinserted into the catheter, the guide marks aligned, and the position of the catheter tip 63 located and/or repositioned using ultrasonic imaging system 100 as described above.

The catheter may comprise a single lumen catheter, but it can have multiple lumens. As noted above, the proximal portion of the catheter may terminate at catheter hub 65. As shown in FIGS. 7 and 8, catheter 60 can be advanced to a target location, such as the superior vena cava 273, or some other site within human body 200, for delivery of fluids such as antibiotics, chemotherapy, pain medicine, nutrition, or for withdrawing blood.

With reference again to FIG. 4, in another aspect of the present invention, ultrasonic imaging system 100 may incorporate suitable software or processing capability for providing an audio or visual signal (in addition to the displayed image of the ultrasonic transmitter) alerting the operator that the distal end of the guidewire is at the desired location or not at the desired location. For example, based on the frequency of the detected ultrasonic transmitter, the image of the ultrasonic transmitter may be color coded, e.g., a red color indicating that the catheter tip has been located and is not in the target location, or a green light indicating that the catheter tip has been located and is in the target location. The user notification signal can also take other forms, including an audio notification or a message display.

The ultrasonic transmitter may resonate at about the same frequency of the ultrasound transmitter/receiver. For example, the ultrasonic transmitter may resonate at a frequency between about 2 MHz and about 18 MHz, and desirably at a frequency of about 910 MHz. The ultrasonic resonator may comprise a piezo film, with an upper electrode, a lower electrode, and a piece of piezo film configured between the upper and lower electrodes. The electrodes may be silver ink screen printed electrodes, which offer high conductivity, high flexibility and a thin profile. The upper electrode and lower electrode overlap at the active piezo film area. When the piezo film is energized, ultrasonic waves may be generated between the upper electrode and lower electrode surfaces at the active piezo film area. The ultrasonic waves may be proportional to the amount of energy provided by the power supply.

Figure 9:
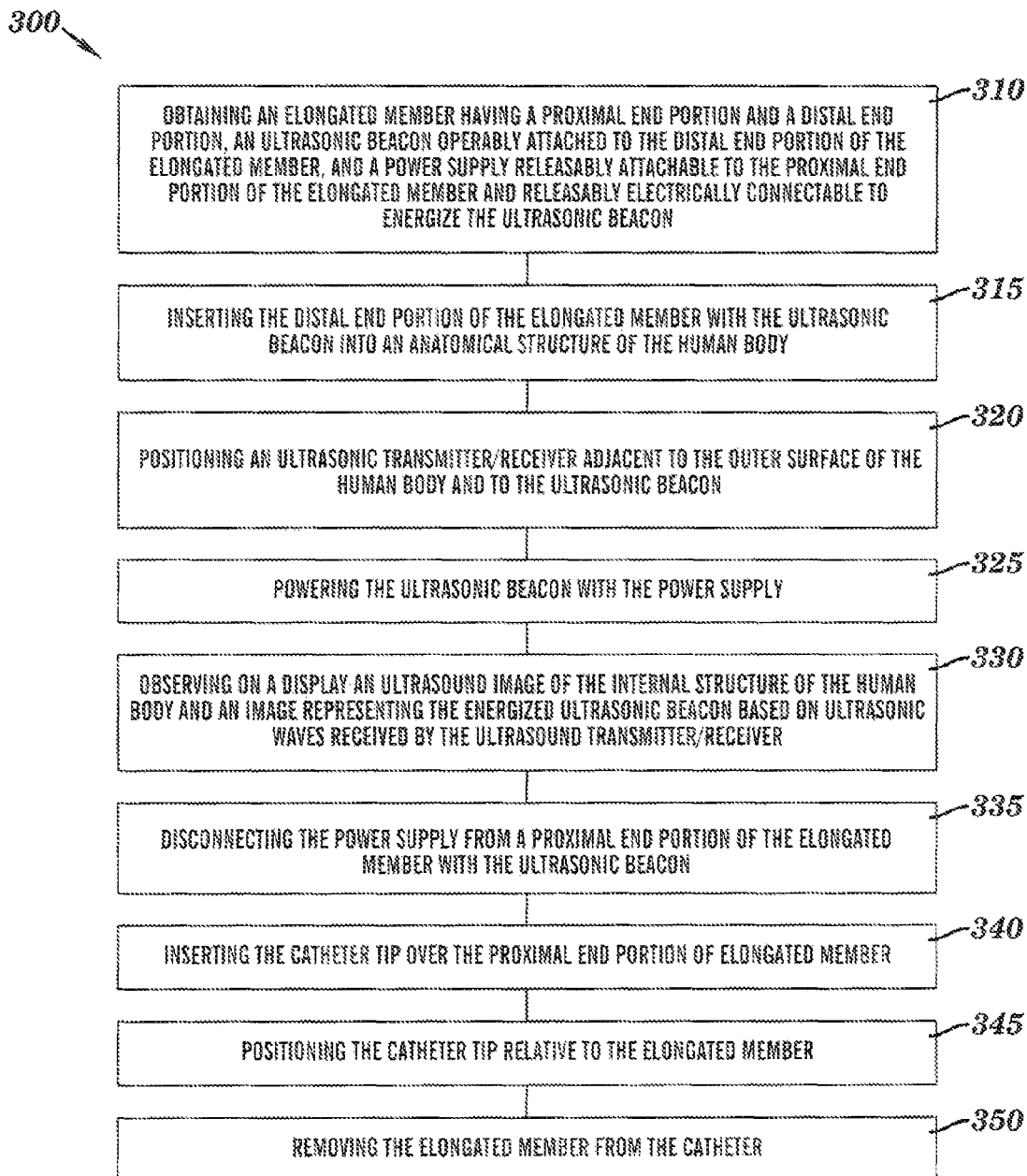
FIG. 9 is a flowchart of one embodiment of a method for positioning a catheter having a tip within a human body in accordance with an aspect of the present invention.

FIG. 9 illustrates one embodiment of a method 300 for positioning a catheter having a tip within a human body in accordance with an aspect of the present invention. For example, an energizable guidewire may be installed first in a human body, then the catheter slid onto the guidewire, and then the guidewire removed.

In particular, method 300 includes at 310, obtaining an elongated member having a proximal end portion and a distal end portion, an ultrasonic beacon operably attached to the distal end portion, and a power supply releasably attachable to the proximal end portion of the elongated member and releasably electrically connectable to energize the ultrasonic beacon. At 315, the distal end portion of the elongated member with the ultrasonic beacon is inserted into an anatomical structure of the human body. An ultrasonic transmitter/receiver is positioned adjacent to the outer surface of the human body and the ultrasonic beacon, at 320, and the ultrasonic beacon is powered with the power supply, at 325. At 330, a display is observed of an ultrasound image of the internal structure of the human body and an image representing the energized ultrasonic beacon based on ultrasonic waves received by the ultrasound transmitter/receiver. The power supply is disconnected from the proximal end portion of the elongated member, at 315, and the catheter tip is inserted over the proximal end portion of elongated member at 340. The catheter tip is positioned relative to the elongated member at 345, and the elongated member is removed from the catheter at 350.

Figure 10:
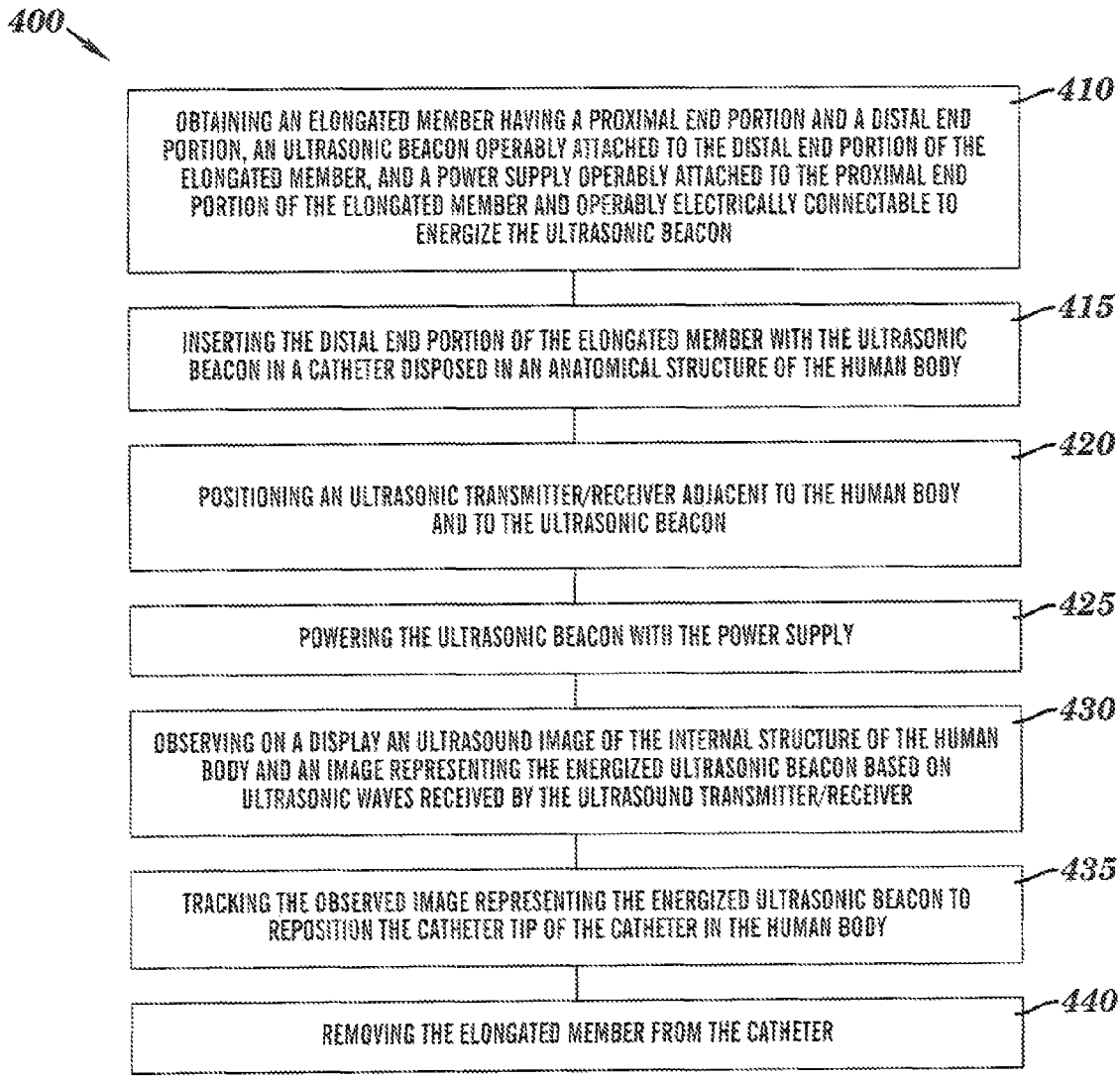
FIG. 10 is a flowchart of an embodiment of a method for repositioning a catheter tip of a catheter within a human body in accordance with an aspect of the present invention.

FIG. 10 illustrates another embodiment of a method 400 for repositioning a catheter tip of a catheter within a human body in accordance with an aspect of the present invention. For example, a catheter tip of a catheter that has already been installed in a human body may be repositioned employing the energized guidewire of the present invention. It will be appreciated that in performing method 400, the power supply may be permanently attached to the proximal end portion of the guidewire as the power supply need not be removed from the guidewire.

In particular, method 400 includes at 410, obtaining an elongated member having a proximal end portion and a distal end portion, an ultrasonic beacon operably attached to the distal end portion of the elongated member, and a power supply operably attached to the proximal end portion of the elongated member and operably electrically connectable to energize the ultrasonic beacon. The distal end portion of the elongated member with the ultrasonic beacon is positioned in a catheter disposed in anatomical structure of the human body, at 415. At 420, an ultrasonic transmitter/receiver is positioned, adjacent to the human body and to the ultrasonic beacon, and at 425, the ultrasonic beacon is powered with the power supply. At 430, a display is observed of an ultrasound image of the internal structure of the human body and an image representing the energized ultrasonic beacon based on ultrasonic waves received by the ultrasound transmitter/receiver. The observed image representing the energized ultrasonic beacon is tracked to reposition the catheter tip of the catheter in the human body at 435, and the elongated member is removed from the catheter at 440.

Figure 11:
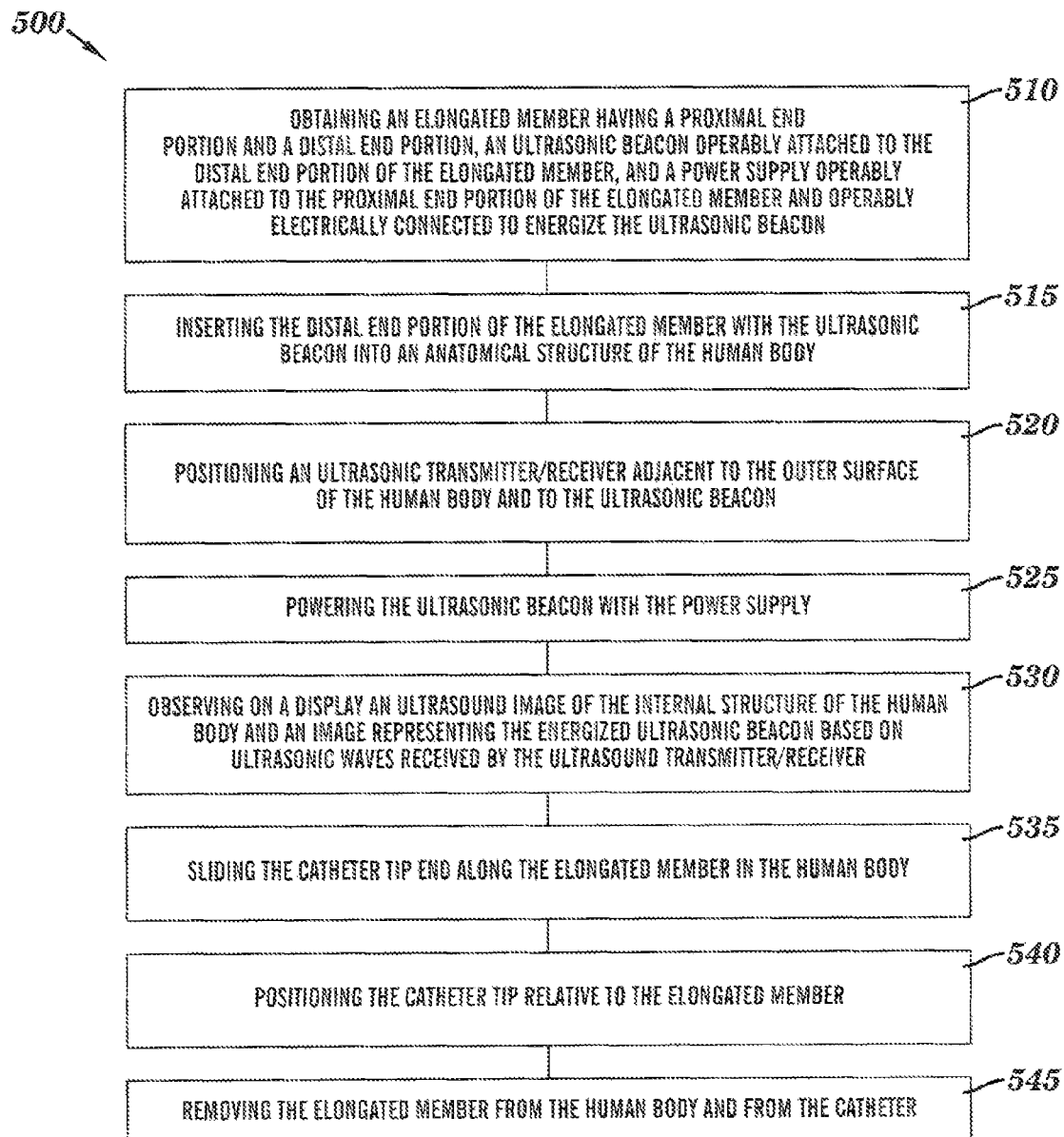
FIG. 11 is a flowchart of an embodiment of a method for positioning a catheter tip of a catheter within a human body in accordance with an aspect of the present invention.

FIG. 11 illustrates another embodiment of a method 500 for positioning a catheter tip of a catheter within a human body in accordance with an aspect of the present invention. In particular, method 500 may include, at 510, obtaining an elongated member having a proximal end portion and a distal end portion, an ultrasonic beacon operably attached to the distal end portion of the elongated member, and a power supply operably attached to the proximal end portion of said elongated member and operably electrically connected to energize the ultrasonic beacon. The distal end portion of the elongated member with the ultrasonic beacon is inserted into an anatomical structure of the human body at 515, and an ultrasonic transmitter/receiver is positioned adjacent to the outer surface of the human body and to the ultrasonic beacon at 520. The ultrasonic beacon is powered with the power supply at 525, and at 530, a display is observed of an ultrasound image of the internal structure of the human body and an image representing the energized ultrasonic beacon based on ultrasonic waves received by the ultrasound transmitter/receiver. At 535, the catheter tip is slid along the elongated member in the human body, and at 540, the catheter tip is positioned relative to the elongated member. At 545, the elongated member is removed from the human body and from the catheter.

For example, as illustrated in FIG. 11, a catheter may be installed on an energizable guidewire having a permanently attached power supply. The energized guidewire may be about twice as long to allow the catheter to be restrained on one end portion of the guidewire as the other end portion of the guidewire is installed in the human body. Thereafter, the catheter may be slid into position in the human body, and then the guidewire removed.

In addition, as illustrated in FIG. 11, the power supply may be releasably attachable to the proximal end of the elongated member and releasably electrically connectable to energize the ultrasonic beacon. The inserting the distal end portion of the elongated member with the ultrasonic beacon into an anatomical structure of the human body may be performed with the power supply is not attached to proximal end portion of said elongated member, and the powering of the ultrasonic beacon, may include attaching the power supply to the proximal end portion of the elongated member.

Figure 12:
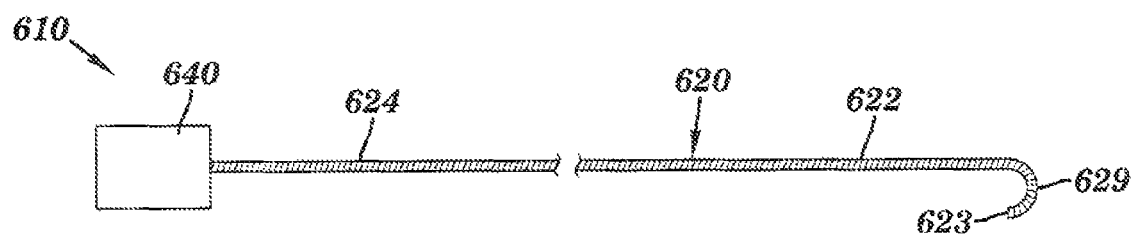
FIG. 12 is a side elevational view of another embodiment of an energizable guidewire in accordance with an aspect of the present invention.

FIG. 12 illustrates another exemplary embodiment of an energizable guidewire 610 in accordance with an aspect of the present invention. For example, guidewire 610 may be essentially the same as guidewire 10 (FIG. 1) as described above with the exception of the distal end portion of the guidewire. Guidewire 610 may include an elongated member 620 and a releasably attachable power supply 640. Elongated member 620 may include a distal end portion 622 and a proximal end portion 624. Distal end portion 622 may terminate in a curved portion 629 such as having a curved J-shaped configuration which terminates in a distal end 623 to reduce the likelihood of damage to internal structures in the body.

Figure 13:
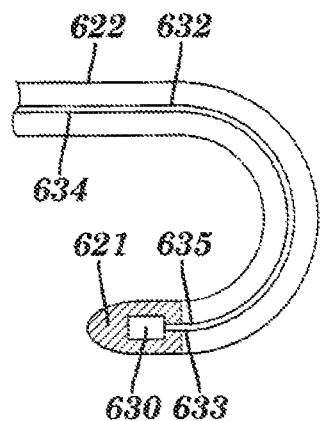
FIG. 13 is an enlarged side elevational view, partially cut away, of the distal end of the energizable guidewire of FIG. 12.

As shown in FIG. 13, adjacent to distal end portion 622 of the elongated member is an ultrasonic beacon 630 such as a piezoelectric transmitter, crystal, or film. Plurality of wires 632 and 634 may be operably electrically connected to the ultrasonic beacon. For example, a distal end portion 633 of wire 632 may be operatively connected to ultrasonic beacon 630, and a distal end portion 635 of wire 634 may be operatively connected to ultrasonic beacon 630. The proximal end of the wires may be connected to a suitable driver and electrical power supply. Distal end portion 622 of the elongated member may be filled with gel or other suitable potting material 621 around beacon 630 to reduce the likelihood of an air cavity attenuating or prevent transmission of ultrasonic waves from beacon 630.

Figure 14:
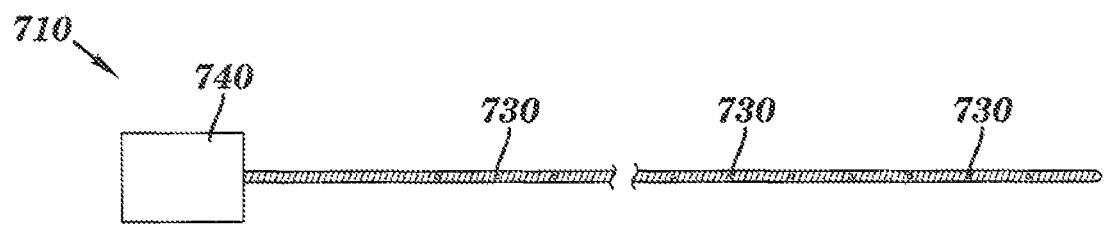
FIG. 14 is a side elevational view of another embodiment of an energizable guidewire having a plurality of ultrasonic beacons in accordance with an aspect of the present invention.
Figure 15:
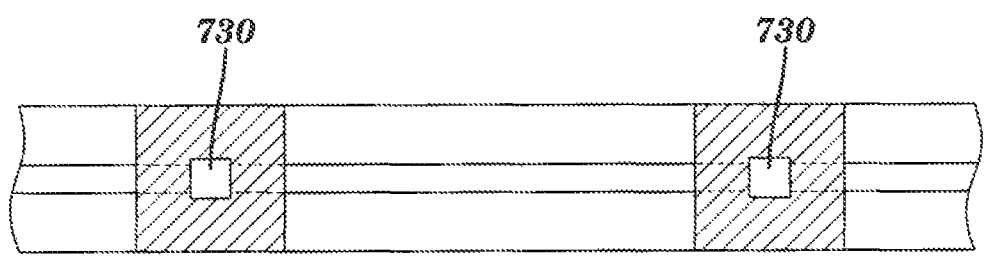
FIG. 15 is an enlarged side elevational view, partially cut away, of a portion of the energizable guidewire of FIG. 14.

FIG. 14 is an embodiment of an energizable guidewire 710 in accordance with an aspect of the present invention. For example, guidewire 710 may be essentially the same as guidewire 10 (FIG. 1) as described above with the exception of having a plurality of spaced-apart ultrasonic beacons 730. The beacons may be spaced apart at regular intervals such as every 1 or 2 centimeters or 10 centimeters. Ultrasonic beacons may be serially electronically connected to power supply as shown in FIG. 14. Alternatively, ultrasonic beacons may be separately connected to power supply 740, and may be operatively configured to emit ultrasonic waves at different frequencies. The plurality of ultrasonic beacons may be evenly spaced-apart at known distances, and used to confirm sizes of anatomical structure or positions in a human body using the ultrasound imaging system.

Some or all of the components mentioned above could be included in a kit, and include instructions for use. In addition, the elongated member noted above may have a "window" at distal end portion of guidewire through which ultrasonic wave may be directed. It will be appreciated that the ultrasonic beacon may be disposed on the outer surface of the elongated member.

The various catheters may be coaxially disposed on an elongated member. The energizable guidewire may be preloaded into the catheter such as a PICC catheter. Typically, the energizable guidewire will be about twice as long as the catheter. In this embodiment, the power supply may be permanently attached to the distal end of the guidewire, e.g., it does not have to be removed to insert the catheter.

Although it is common to have the catheter tip terminate in a lower ⅓ of the superior vena cava, or at the junction of the superior vena cava and the right atrium, the method according to the present invention can be used for procedures that target any site within the body. Further, any type of catheter tip can be positioned, including acute and chronic dialysis catheters, subcutaneous port catheters, and central venous catheters. In addition, access sites do not need to be in the arm. For example, for a patient with amputated arms, the access site may be in the groin or in the back.

From the description above, it will be appreciated that several advantages of one or more aspects of the present invention include:

a) enhanced imaging capabilities using the energized guidewire and standard ultrasound imaging systems producing a readily observable image of the ultrasonic beacon on a display compared to simply imaging the catheter alone with standard ultrasound imaging systems;

b) not require specialized ultrasound transmitter receivers or other capital equipment as the present invention employs standard ultrasound imaging systems;

c) no specialized training required;
d) determine location of catheter tip even if mispositioned;
e) use with any PICC, dialysis catheter, other central venous catheter, or other catheters, even previously placed catheters;
f) use as a standard guidewire for initial PICC placement and then as a tip locator;
g) use with any catheter regardless of length, size or manufacturer;
h) eliminates a separate stylet component, or separate electromagnetic detecting and separate processing capability for superimposing the location of the ultrasonic transmitter on the ultrasonic image;
i) reduces operator and patient exposure to harmful radiation such as X-ray radiation;
j) because the beacon (transmitter) is passive in only transmitting ultrasonic waves and not operable for receiving or detecting ultrasonic waves the size of the guidewire may be small compared to guidewires having thereby eliminating additional wiring/components for receiving and detecting ultrasonic waves;
k) overcoming problems with electrocardiogram detection which require a normal sinus rhythm, and cannot indicate when the catheter tip is in locations including the jugular vein and the subclavian;
l) reduced costs in manufacture and equipment compared to prior art locating techniques;
m) increasing the number of facilities equipped to perform catheter insertion and maintenance procedures compared to prior art locating techniques;
n) operable with patients having pacemakers or skin disorders, or other ailments.

Thus, while various embodiments of the present invention have been illustrated and described, it will be appreciated to those skilled in the art that many changes and modifications may be made thereunto without departing from the spirit and scope of the invention.

The invention claimed is:
1. A catheter assembly comprising:
an elongated member having a proximal end portion and a distal end portion,
an ultrasonic beacon operably attached to said distal end portion of said elongated member;
a power supply releasably attachable to said proximal end portion of said elongated member and releasably electrically connectable to said ultrasonic beacon; and
a catheter comprising a proximal end portion and a distal end portion, said distal end portion of said catheter being slideably receivable over said proximal end portion of said elongated member when said power supply is detached from said elongated member.

2. The catheter assembly of claim 1 wherein said proximal end portion of said elongated member comprises a plurality of contacts operable for engaging a plurality of contact on said power supply.

3. The catheter assembly of claim 1 wherein said proximal end portion of said elongated member comprises a plurality of spaced-apart contacts, and said power supply comprises a cavity for receiving said proximal end portion of said elongated member comprising said plurality of spaced-apart contacts.

4. The catheter assembly of claim 1 wherein said power supply comprises a driver for driving said ultrasonic beacon.

5. The catheter assembly of claim 1 wherein said driver comprises oscillator.

6. The catheter assembly of claim 1 wherein said elongated member comprises aligning marks for positioning the catheter relative to the elongated member.

7. The catheter assembly of claim 1 wherein the elongated member has a plurality of other spaced-apart ultrasonic beacons.

8. The catheter assembly of claim 1 wherein said elongated member comprises at least one of a guidewire, a stylet, an inner catheter, and a guide catheter.

9. The catheter assembly of claim 8 wherein said distal end portion of said elongated member comprises a curved distal end.

10. An ultrasonic tip location system comprising:
an elongated member having a proximal end portion and a distal end portion, and adapted to be inserted into a blood vessel of a human body;
an ultrasonic beacon positioned at the distal end portion of the elongated member and operable to be powered by a power supply to generate ultrasonic waves to be detected by an ultrasound receiver outside of the human body;
a catheter having a proximal end portion and a distal end portion being slideably receivable over the proximal end portion of the elongated member.

11. The ultrasonic tip location system of claim 10, wherein the elongated member includes a plurality of uniformly spaced aligning marks for positioning the catheter relative to the elongated member.

12. The ultrasonic tip location system of claim 10, wherein the elongated member has at least one other ultrasonic beacon spaced by a known distance from the ultrasonic beacon at the distal end portion of the elongated member.

13. The ultrasonic tip location system of claim 10, wherein the elongated member includes a guidewire or a stylet.

14. The ultrasonic tip location system of claim 10 wherein the distal end portion of the elongated member has a curve.

15. The ultrasonic tip location system of claim 10, wherein the elongated member includes potting material surrounding and covering the ultrasonic beacon at the distal end portion of the elongated member.

* * * * *